United States Patent
Yasukawa et al.

(10) Patent No.: US 10,464,860 B2
(45) Date of Patent: Nov. 5, 2019

(54) METHOD FOR PRODUCING ISOBUTYLENE FROM ISOBUTANOL

(71) Applicant: Mitsubishi Chemical Corporation, Tokyo (JP)

(72) Inventors: Toshiya Yasukawa, Otake (JP); Tatsuya Suzuki, Otake (JP); Akio Takeda, Otake (JP); Wataru Ninomiya, Otake (JP); Kenichi Miyaki, Otake (JP); Ken Ooyachi, Otake (JP); Shuji Akihara, Sapporo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 26 days.

(21) Appl. No.: 15/307,614

(22) PCT Filed: May 1, 2015

(86) PCT No.: PCT/JP2015/063110
§ 371 (c)(1),
(2) Date: Oct. 28, 2016

(87) PCT Pub. No.: WO2015/170686
PCT Pub. Date: Nov. 12, 2015

(65) Prior Publication Data
US 2017/0050896 A1 Feb. 23, 2017

(30) Foreign Application Priority Data

May 7, 2014 (JP) ................................. 2014-095675
Aug. 20, 2014 (JP) ................................. 2014-167032

(51) Int. Cl.
*C07C 1/24* (2006.01)
(52) U.S. Cl.
CPC ............ *C07C 1/24* (2013.01); *C07C 2521/04* (2013.01)

(58) Field of Classification Search
CPC .............................. C07C 1/24; C07C 2521/04
See application file for complete search history.

(56) References Cited

U.S. PATENT DOCUMENTS 5,475,183 A 12/1995 Araki et al.
2011/0087000 A1 4/2011 Peters et al.
(Continued)

FOREIGN PATENT DOCUMENTS

FR 2 988 717 A1 10/2013
FR 2988718 A1 * 10/2013 .............. B01J 21/12
(Continued)

OTHER PUBLICATIONS

Beattie et al. ("Vapor Pressures and Critical Constants of Isobutene" Journal of the American Chemical Society vol. 64, No. 3 (1942): 546-548) (Year: 1942).*
(Continued)

*Primary Examiner* — Brian A McCaig
*Assistant Examiner* — Jason Y Chong
(74) *Attorney, Agent, or Firm* — Oblon, McClelland, Maier & Neustadt, L.L.P.

(57) ABSTRACT

The purpose of the present invention is to provide a method that can produce, with high yield or high selectivity isobutylene by means of isobutanol dehydration-reaction. An isobutylene production method of a first embodiment of the present invention is a method for producing isobutylene by means of isobutanol dehydration-reaction, wherein isobutanol is reacted using a catalyst for which the BET specific surface area is within the range of 60 m²/g-175 m²/g, and the reaction is carried out under a reaction pressure of 50 kPa-750 kPa as the absolute pressure. An isobutylene production method of a second embodiment of the present invention includes: using a catalyst which is filled into a reaction chamber and for which the particle diameters of at (Continued)

least 90 mass % of the catalyst are within the range of 700 μm-1000 μm; setting the isobutanol concentration within a supplied reaction gas to 30 vol %-85 vol %; setting the weight hourly velocity (WHSV) of the isobutanol to 0.175 $h^{-1}$~20 $h^{-1}$; and reacting isobutanol under a reaction pressure of 50 kPa-750 kPa as the absolute pressure.

15 Claims, 4 Drawing Sheets

(56) References Cited

U.S. PATENT DOCUMENTS

| | | |
|---|---|---|
| 2011/0172475 A1 | 7/2011 | Peters et al. |
| 2013/0204057 A1 | 8/2013 | Adam et al. |
| 2013/0261323 A1 | 10/2013 | Peters et al. |
| 2014/0107387 A1 | 4/2014 | Yamaguchi et al. |
| 2014/0296596 A1 | 10/2014 | Chaumonnot et al. |
| 2014/0303419 A1 | 10/2014 | Boll et al. |
| 2015/0057481 A1 | 2/2015 | Chaumonnot et al. |

FOREIGN PATENT DOCUMENTS

| | | |
|---|---|---|
| JP | 4-247043 A | 9/1992 |
| JP | 2013-506717 A | 2/2013 |
| JP | 2013-516487 A | 5/2013 |
| JP | 2013-522270 A | 6/2013 |
| WO | WO 2011/044243 A1 | 4/2011 |
| WO | WO 2011/085223 A1 | 7/2011 |
| WO | WO 2011/113834 A1 | 9/2011 |
| WO | WO 2013/057145 A1 | 4/2013 |
| WO | WO 2013/144491 A1 | 10/2013 |
| WO | WO 2014/118484 A1 | 8/2014 |

OTHER PUBLICATIONS

International Search Report dated Aug. 11, 2015 in PCT/JP2015/063110 filed May 1, 2015.
Elibieta Sikora, et al., "Study of methanol and isobutanol coupling over acid catalysts" Reaction Kinetics and Catalysis Letters, vol. 80, 2003, pp. 189-197.
Owen C. Feeley, et al., "Isobutene from isobutanol/methanol mixtures over inorganic acid catalysts" American Chemical Society, Division of Fuel Chemistry, vol. 37, No. 4, 1992, pp. 1817-1824.
Joshua D. Taylor, et al., Dehydration of Fermented Isobutanol for the Production of Renewable Chemicals and Fuels Topics in Catalysis, vol. 53, No. 15-18, Sep. 2010, 9 Pages.
Korean Office Action dated Jan. 29, 2018 in Korean Patent Application No. 10-2016-7027539 (with unedited computer generated English translation). citing documents AA and AO therein, 9 pages.

* cited by examiner

[Fig. 1]
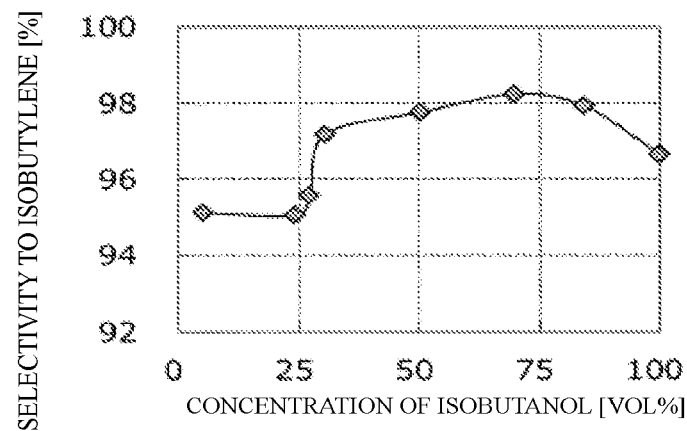
[Fig. 2]
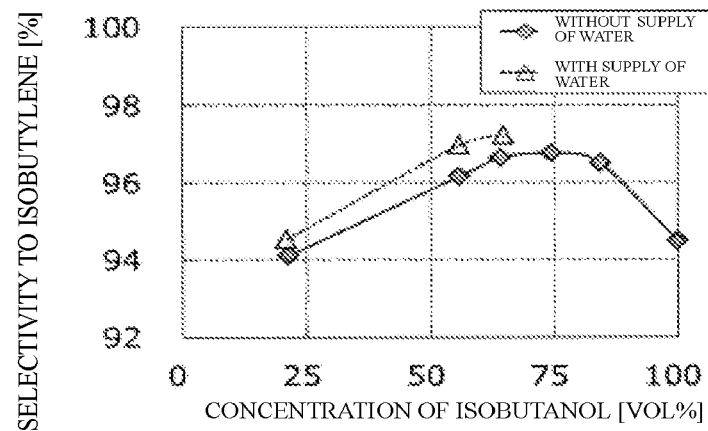

[Fig. 3]
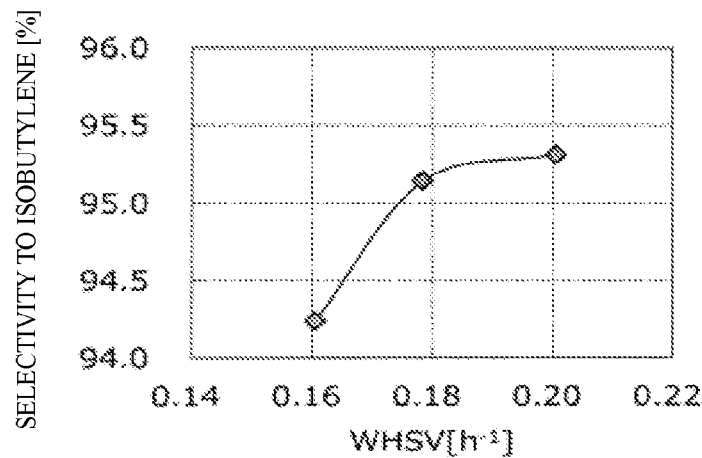
[Fig. 4]
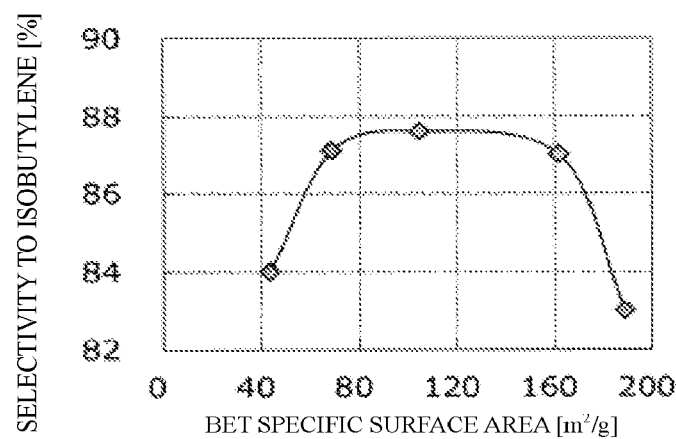

[Fig. 5]
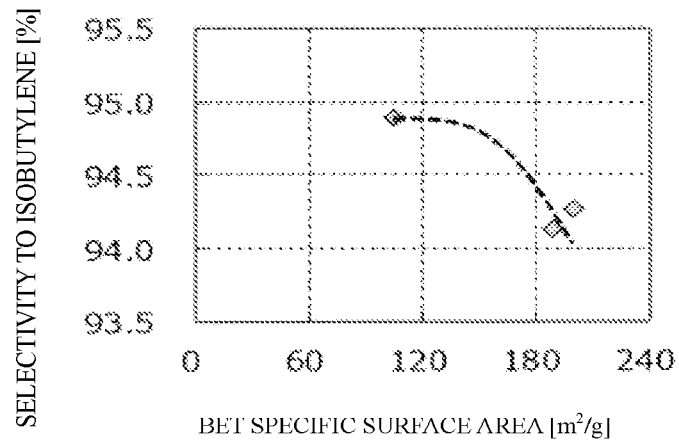
[Fig. 6]
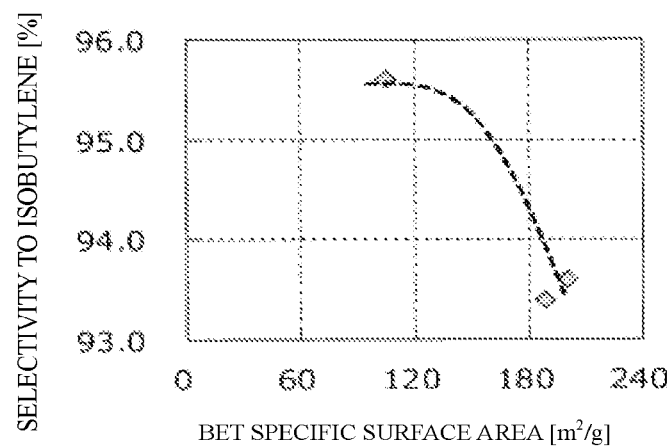

[Fig. 7]
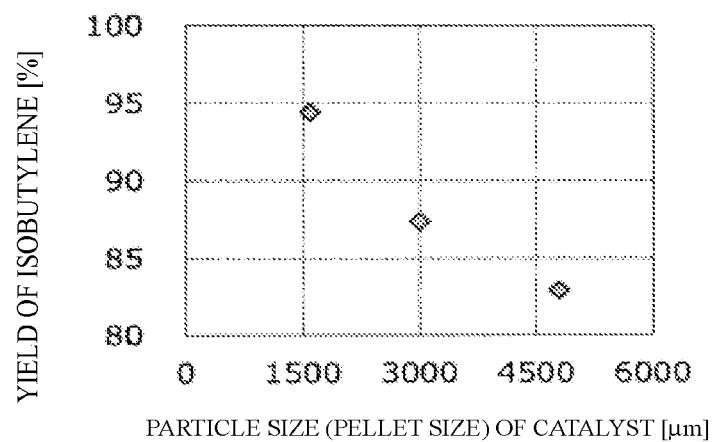
[Fig. 8]
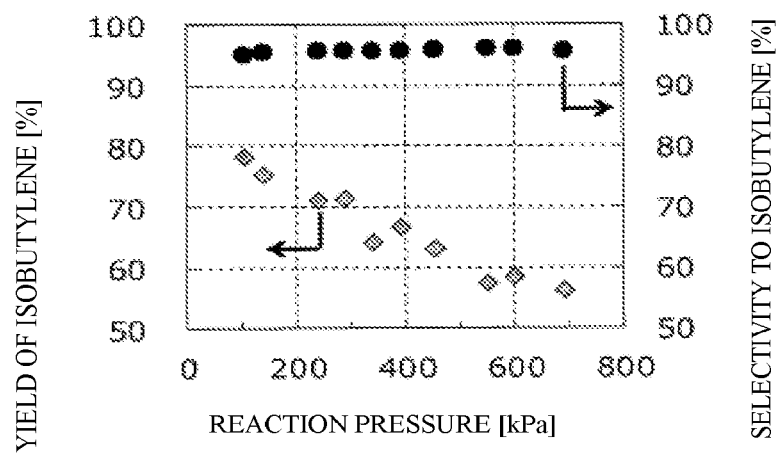

METHOD FOR PRODUCING ISOBUTYLENE FROM ISOBUTANOL

TECHNICAL FIELD

The present invention relates to a method for producing isobutylene from isobutanol, particularly biomass-derived isobutanol.

BACKGROUND ART isobutylene is one of the important chemical raw materials that are converted into ethyl tert-butyl ether (ETBE), paraxylene, and a methyl methacrylate (MMA) monomer. Among these, for example, the MMA monomer is a substance with significantly high utility value as a raw material for poly(methyl methacrylate) that is useful as a transparent resin. There is a method, as one of the methods for producing the MMA monomer, to synthesize this MMA monomer by using isobutylene as a starting material.

Isobutylene as a raw material for the MMA monomer is obtained by extracting isobutylene as tert-butanol from the spent BB that is a residue obtained by the fractional distillation of butadiene from the C4 fraction obtained by naphtha cracking by the hydration reaction using an acid catalyst and dehydrating this. In addition, there is also a method in which methyl tert-butyl ether is once synthesized from isobutylene in the spent BB and methanol and is then decomposed. Such a current method for producing isobutylene uses petroleum as a raw material. Hence, the development of a novel method which does not depend on petroleum is desired in the recent situation that the depletion of petroleum is concerned.

In addition, carbon dioxide generated when petroleum is burned is regarded as a cause of global warming. Thus, the biorefinery technology has attracted the worldwide attention as an energy and chemical producing technology from biomass of a renewable resource. The biorefinery is a technology to produce synthesis gas, saccharides such as glucose, and aromatic compounds such as lignin by the gasification, saccharification, and extraction of various kinds of biomass and to produce energy and chemicals by converting them in various ways. Examples of the product that is produced by the biorefinery may include ethanol, butanol, or diesel oil as energy. In chemicals, it is possible to produce a significantly great number of chemicals by the derivation from key compounds (platform compounds) such as saccharide-derived succinic acid, 3-hydroxypropionic acid, and aspartic acid proposed by the US Department of Energy.

Meanwhile, isobutanol is also known to be produced by fermenting glucose and mentioned as one of the biomass-derived raw materials. It is described in, for example, Patent Literature 1, Patent Literature 2, Patent Literature 3, Patent Literature 4, Patent Literature 5, and Non-Patent Literature 1 that isobutylene can be produced by dehydrating isobutanol.

CITATION LIST

Patent Literature

Patent Literature 1: WO 2011/085223 A
Patent Literature 2: JP 4-247043 A
Patent Literature 3: JP 2013-506717 W
Patent Literature 4: JP 2013-516487 W
Patent Literature 5: JP 2013-522270 W

Non-Patent Document

Non-Patent Literature 1: Topics in Catalysis (2010) 53, 1224-1230

SUMMARY OF THE INVENTION

Problem to be Solved by the Invention

Isobutylene is produced through the dehydration of isobutanol by using, as the dehydration catalyst, γ-alumina or zeolite in Patent Literature 1, Patent Literature 3, Patent Literature 4, and Patent Literature 5, γ-alumina in Non-Patent Literature 1, and γ-alumina containing silica in Patent Literature 2. However, the selectivity to isobutylene in the gas components after the reaction is not always sufficient.

In order to cut down the cost for the production of isobutylene, it is required to decrease the amount of the catalyst used with respect to the amount of required isobutanol treated in order to obtain desired isobutylene or to advance the dehydration reaction at a higher selectivity. In addition, it is required to advance the dehydration reaction at a high reaction efficiency and a high selectivity in the same manner as above in order to efficiently utilize the raw material for the purpose of decreasing the environmental burden.

The invention has been achieved to solve such a problem. In other words, the object of the invention is to provide a method for producing isobutylene in a high yield or at a high selectivity by the dehydration reaction of isobutanol.

Solution to Problem

The first invention is a method for producing isobutylene by dehydration reaction of isobutanol, in which isobutanol is reacted at a reaction pressure of 50 kPa or more and 750 kPa or less as an absolute pressure by using a catalyst having a BET specific surface area in a range of 60 m$^2$/g or more and 175 m$^2$/g or less.

In addition, the second invention is a method for producing isobutylene by dehydration reaction of isobutanol, in which isobutanol is reacted at a concentration of isobutanol in a reaction gas to be supplied of 30 vol % or more and 85 vol % or less, a weight hourly space velocity (WHSV) of isobutanol of 0.175 h$^{-1}$ or more and 20 h$^{-1}$ or less, and a reaction pressure of 50 kPa or more and 750 kPa or less as an absolute pressure by using a catalyst of which 90 mass % or more has a particle size in a range of 700 μm or more and 10000 μm or less.

In addition, in the first invention, it is preferable that 90 mass % or more of a catalyst have a particle size in a range of 700 μm or more and 10000 μm or less and the weight hourly space velocity (WHSV) of isobutanol in a reaction gas to be supplied be 0.175 h$^{-1}$ or more and 20 h$^{-1}$ or less.

In addition, in the second invention, it is preferable that the concentration of isobutanol be 55 vol % or more and 80 vol % or less.

Advantageous Effect of Invention

According to the invention, it is possible to produce isobutylene in a high yield or at a high selectivity by the dehydration reaction of isobutanol. Furthermore, in the present invention, it is possible to produce isobutylene at a high selectivity particularly by using biomass-derived isobutanol as a starting material, and thus the invention is useful from the viewpoint of environmental protection as well.

BRIEF DESCRIPTION OF DRAWINGS

FIG. 1 is a graph illustrating the relation between the concentration of isobutanol of the raw material in the reaction gas and the selectivity to isobutylene in Examples 1 to 4 and Comparative Examples 1 to 4 (reaction temperature: 300 to 301° C.);

FIG. 2 is a graph illustrating the relation between the concentration of isobutanol of the raw material in the reaction gas and the selectivity to isobutylene in Examples 5 to 10 and Comparative Examples 5 to 7 (reaction temperature: 340 to 341° C.);

FIG. 3 is a graph illustrating the relation between the WHSV and the selectivity to isobutylene in Examples 11 and 12 and Comparative Example 8;

FIG. 4 is a graph illustrating the relation between the BET specific surface area and the selectivity to isobutylene in Examples 13 to 15 and Comparative Examples 9 and 10;

FIG. 5 is a graph illustrating the relation between the BET specific surface area and the selectivity to isobutylene in Example 16 and Comparative Examples 11 and 12;

FIG. 6 is a graph illustrating the relation between the BET specific surface area and the selectivity to isobutylene in Example 17 and Comparative Examples 13 and 14;

FIG. 7 is a graph illustrating the relation between the particle size (pellet size) of catalyst and the yield of isobutylene in Examples 18 to 20; and FIG. 8 is a graph illustrating the relation between the reaction pressure and the selectivity and yield of isobutylene in Examples 21 to 30.

DETAILED DESCRIPTION OF PREFERRED EMBODIMENTS

In the invention, isobutylene is produced by the dehydration reaction of isobutanol. Isobutanol of the starting material is not particularly limited. However, it is preferable to use biomass-derived isobutanol from the viewpoint of environmental protection.

Biomass-derived isobutanol is one that is purified from an organic compound obtained through the fermentation process using a fermentable saccharide of biomass, or it is isobutanol that is obtained by the process including any one or more of the catalytic chemical conversion or thermochemical conversion of biomass. Biomass is briefly divided into those derived from resource crops and those derived from waste. The biomass derived from resource crops are, for example, a food crops, wood, and flowering plants, and the unused parts of those crops can also be used. On the other hand, examples of the biomass derived from waste may include food waste, sludge such as sewage, livestock manure, and waste paper.

The dehydration reaction of isobutanol may be conducted in either of a liquid phase or a gas phase. It is possible to utilize the form of gas phase reaction represented by the fixed bed and the fluidized bed in the case of conducting the reaction in a gas phase. Hereinafter, a case in which the reaction is conducted in a gas phase will be described, but the invention is not limited thereto.

It is preferable to supply the raw material to the reactor by being evaporated in advance. The evaporator for evaporating the raw material is not particularly limited. For example, it is possible to use various kinds of evaporators such as a jacket type, a natural circulation horizontal tube type, a natural circulation immersing tube type, a natural circulation vertical short tube type, a long vertical tube rising film type, a horizontal tube falling film type, a forced circulation horizontal tube type, a forced circulation vertical tube type, and a coil type. In addition, it is also possible to employ a method in which a beating coil is simply wrapped around a pipe and the raw material is evaporated in the raw material supply pipe before being introduced into the reactor and supplied to the reactor in a gaseous state. Furthermore, the evaporator is not particularly limited in a case in which the component other than the raw material is supplied to the reactor by being evaporated as well.

In the case of supplying isobutanol of a raw material to the reactor, the concentration of isobutanol in the reaction gas can be adjusted by using a diluent gas. The kind of diluent gas is not particularly limited. For example, oxygen can be used as a diluent gas in a concentration which is out of the explosive range and in which a side reaction is not significantly promoted. In addition, hydrogen can be used as a diluent gas in a concentration in which a side reaction is not significantly promoted in the concentration range in which hydrogen can be safely operated. Furthermore, it is possible to suitably use one or more kinds selected from the group consisting of nitrogen, helium, neon, krypton, xenon, radon, argon, methane, ethane, propane, butane, isobutane, carbon monoxide, carbon dioxide, nitrogen monoxide, nitrogen dioxide, nitrous oxide, dinitrogen trioxide, dinitrogen tetraoxide, dinitrogen pentaoxide, and water vapor as a diluent gas.

The first embodiment of the method for producing isobutylene by dehydration reaction of isobutanol according to the first invention is a method for producing isobutylene at the reaction pressure of 50 kPa or more and 750 kPa or less as the absolute pressure by using a catalyst of which the BET specific surface area calculated from the $N_2$ adsorption-desorption isotherm is in a range of 60 $m^2/g$ or more and 175 $m^2/g$ or less.

It is preferable to use the catalyst by filling it in the reactor. The lower limit of the BET specific surface area calculated from the $N_2$ adsorption-desorption isotherm of the catalyst for dehydration is 60 $m^2/g$ or more, preferably 65 $m^2/g$ or more, and more preferably 69 $m^2/g$ or more. In addition, the upper limit of the BET specific surface area calculated from the $NT_2$ adsorption-desorption isotherm of the catalyst for dehydration to be filled in the reactor is 175 $m^2/g$ or less, preferably 170 $m^2/g$ or less, and more preferably 162 $m^2/g$ or less. In a case in which the BET specific surface area is less than 60 $m^2/g$, the activity as a catalyst tends to decrease and thus a great amount of catalyst is required. On the other hand, in a case in which the BET specific surface area is greater than 175 $m^2/g$, the production of linear butenes of a by-product is promoted and thus the selectivity to isobutylene decreases. Incidentally, the BET specific surface area is a value measured by using the TriStar 3000 (trade name, manufactured by Shimadzu Corporation).

The lower limit of the reaction pressure during the dehydration reaction of isobutanol is 50 kPa or more, preferably 75 kPa or more, and more preferably 100 kPa or more as the absolute pressure. On the other hand, the upper limit of the reaction pressure during the dehydration reaction of isobutanol is 750 kPa or less, preferably 700 kPa or less, and more preferably 650 kPa or less as the absolute pressure. Usually, the reactivity is affected by the reaction pressure in the catalyst layer (reaction field), and thus it is desirable to monitor the pressure in the catalyst layer, but the pressure may be measured by the pressure sensor installed at the reactor inlet in a case in which it is difficult to attach the sensor because of the process. In the present application, the pressure at the reactor inlet is defined as the numerical value of the pressure sensor installed at the position at which the influence of pressure loss is negligible. In a case in which the reaction pressure is less than 50 kPa, the equipment for reducing the pressure in the reaction system is required and the cost of equipment is required. In addition, it is disadvantageous in a case in which the reaction pressure exceeds 750 kPa since the reactivity per unit mass of catalyst decreases, and thus it is required to increase the amount of catalyst and a reactor having a greater volume is required in association with it. Incidentally, the range of the reaction pressure is the same in the second invention as well.

The second embodiment of the method for producing isobutylene by dehydration reaction of isobutanol according to the second invention is a method for producing isobutylene, in which isobutanol is reacted at a concentration of isobutanol in the reaction gas to be supplied of 30 vol % or more and 85 vol % or less, a weight hourly space velocity (WHSV) of isobutanol of 0.175 $h^{-1}$ or more and 20 $h^{-1}$ or less, and a reaction pressure of 50 kPa or more and 750 kPa or less as the absolute pressure by using a catalyst of which 90 mass % or more has a particle size in a range of 700 μm or more and 10000 μm or less.

It is preferable to use the catalyst by filling it in the reactor. The lower limit of the range of particle size in which 90 mass % or more of the dehydration catalyst is included is 700 μm or more, preferably 800 μm or more, and more preferably 1000 μm or more. The upper limit of the range of particle size in which 90 mass % or more of the dehydration catalyst is included is 10000 μm or less, preferably 9500 μm or less, and more preferably 9000 μm or less. The size of the mesh of the sieve used is defined as the particle size in a case in which the particle size of the dehydration catalyst is sieved with a sieve or the like. In addition, in the case of a molded catalyst, the diameter is defined as the particle size, for example, in the case of a cylindrical pellet. In a case in which there are a great number of catalysts which have a particle size of less than 700 μm, the pressure loss in the catalyst layer filled in the reactor increases and the cost of equipment and energy for circulating the reaction gas increases. In addition, a decrease in reactivity is caused since the reaction pressure increases. In addition, it is disadvantageous in a case in which there are a great number of catalysts which have a particle size of more than 10000 μm since the effectiveness factor of catalyst decreases and a decrease in activity per unit mass of catalyst is caused. It is preferable that the range of the particle size be satisfied in the first embodiment as well. Incidentally, whether 90 mass % or more of the catalyst has a particle size in the range of 700 μm or more and 10000 μm or less is determined by measuring the outer diameter and length of 100 molded bodies with calipers with regard to the molded catalyst. In addition, it is preferable that the range of particle size of the catalyst be satisfied in the first invention as well.

The lower limit of the concentration of isobutanol in the reaction gas to be supplied for the reaction is 30 vol % or more, preferably 50 vol % or more, and more preferably 55 vol % or more. On the other hand, the upper limit of the concentration of isobutanol in the reaction gas to be supplied for the reaction is 85 vol % or less, preferably 82.5 vol % or less, and more preferably 80 vol % or less. When the concentration of isobutanol exceeds 85 vol %, the side reaction is likely to proceed and the selectivity to isobutylene by the dehydration reaction of isobutanol decreases. Furthermore, in a case in which unreacted isobutanol containing water of a by-product is recovered, the concentration of isobutylene is increased to a high concentration, and it is reused, it is required to separate isobutanol from water and energy for this operation is required. On the other hand, when the concentration of isobutanol is less than 30 vol %, the isomerization reaction is accelerated and the selectivity to isobutylene decreases. Furthermore, the reactor having a greater volume is required so as to increase the cost of equipment and the cost of energy for the recovery of an active component having a thin concentration increases. In addition, it is preferable that water concentration in the reaction gas to be supplied to the reactor is 0.1 vol % or more and 70 vol % or less. By containing water in the reaction gas, it is possible to expect the effect of decreasing the selectivity to a by-product due to the suppression of acid strength of the catalyst.

The lower limit of the weight hourly space velocity (WHSV) of isobutanol with respect to the dehydration catalyst is 0.175 $h^{-1}$ or more, preferably 0.2 $h^{-1}$ or more, and more preferably $0.25^{-1}$ or more. On the other hand, the upper limit of the weight hourly space velocity (WHSV) of isobutanol with respect to the dehydration catalyst is 20 $h^{-1}$ or less, preferably 18 $h^{-1}$ or less, and more preferably 16 $h^{-1}$ or less. In a case in which the WHSV is less than 0.175 $h^{-1}$, a great amount of catalyst is required, a reactor having a greater volume is required in association with that, the equipment increases in size, and the cost of catalyst increases. In addition, in the case of decreasing the amount of isobutanol supplied as well, there is a case in which the WHSV decreases so as to be less than 0.175 $h^{-1}$, and in this case, productivity (yield per unit time and volume) of isobutylene decreases since the amount treated per unit time is too small. On the other hand, it is disadvantageous in a case in which the WHSV exceeds 20 $h^{-1}$ since the amount of isobutanol to be supplied with respect to the amount of catalyst is too great, and thus, in association with a decrease in the conversion ratio of isobutanol, the cost to recover unreacted isobutanol and to recycle it as the reaction raw material increases. It is preferable that the range of WHSV be satisfied in the first embodiment as well. Incidentally, the WHSV is a value defined by the equation to be described later. In addition, it is preferable that the range of WHSV be satisfied in the first invention as well.

It is preferable that the reaction temperature (the temperature in the catalyst layer during the reaction) be in a range of from 108 to 500° C. From the viewpoint of sufficiently obtaining the effect of the invention, the lower limit of the reaction temperature is more preferably 115° C. or higher and even more preferably 150° C. or higher. On the other hand, the upper limit of the reaction temperature is more preferably 415° C. or lower and even more preferably 400° C. or lower. In a case in which the reaction temperature is 500° C. or lower, the reaction rate of the isomerization reaction is suppressed and thus the selectivity to isobutylene of the intended product is improved. On the other hand, in a case in which the reaction temperature is 108° C. or higher, it is less required to increase the amount of the dehydration catalyst or to lower the supply rate of the reaction gas, and thus it is advantageous from the viewpoint of cost or productivity as well. The dehydration reaction of isobutanol is an endothermic reaction, and the method for controlling the reaction temperature is not particularly limited. Here, the reaction temperature is defined as the lowest temperature among the temperatures in the catalyst layer which can be confirmed after the steady state is achieved. Hence, it is desirable to increase the points of measurement or to continuously measure the temperature in the catalyst filling direction in a case in which there is a temperature distribution in the catalyst layer.

It is preferable that the dehydration reaction of isobutanol be conducted by using a dehydration catalyst such as an acid catalyst. Specific examples of the acid catalyst may include alumina, silica-alumina, solid phosphoric acid, titania, and zirconia. Two or more kinds of these may be concurrently used. It is preferable to use alumina particularly from the viewpoint of selectivity to isobutylene.

The crystal morphology of alumina is not particularly limited. Specific examples thereof may include various kinds of alumina such as α-alumina, β-alumina, γ-alumina, σ-alumina, θ-alumina, δ-alumina, and alumina hydrate. Two or more kinds of these may be concurrently used. In the case of concurrently using two or more kinds, those having different crystal morphologies may be mixed together or they may have a crystal state of a mixed phase, and they are not particularly limited. A catalyst containing γ-alumina is preferable particularly from the viewpoint of activity and selectivity.

Alumina may be produced by a known method, and the production method thereof is not particularly limited. For example, it can be easily produced by a thermal decomposition method, a precipitation method, a deposition method, a kneading method, or a method which concurrently uses these methods. Examples of the raw material for alumina may include materials to produce alumina or alumina hydrate by heating or hydrolysis such as a nitrate, an acetate, an alkoxide, a sulfate, a chloride, alkali aluminate, and alum. Examples of the alkali used in the hydrolysis reaction may include caustic alkali, an alkali carbonate, ammonia water, and ammonium carbonate.

Alumina obtained by the method as described above may be used by being molded if necessary. For example, in the case of a gas phase fixed bed reaction, it is preferable to determine the shape of the molded body in consideration of the pressure loss or the diffusion of gas in the reactor. Furthermore, it is preferable to determine the shape of the molded body in consideration of the reaction conditions or the mass transfer in either of the gas phase fluidized bed reaction or the liquid phase reaction. Examples of the method for molding alumina may include a method to mold alumina into an arbitrary shape such as a spherical shape, a ring shape, a cylindrical shape, or a star shape by using a molding machine for powder such as a tablet molding machine, an extrusion molding machine, or an oscillating granulator. In addition, the catalyst thus obtained may be ground so as to be used as a powder. An additive may be mixed with alumina before being molded if necessary. In addition, the BET specific surface area of alumina can be adjusted by changing the temperature to calcine the alumina precursor. Hence, this makes it possible to adjust the BET specific surface area of the catalyst. The calcination temperature for the alumina precursor is preferably from 400 to 1200° C. The BET specific surface area is increased by lowering the calcination temperature, and the BET specific surface area is decreased by increasing the calcination temperature.

The catalyst according to the first invention may contain a compound other than alumina. However, the content of $SiO_2$ in the catalyst is preferably less than 1.0 mass %, more preferably less than 0.75 mass %, and even more preferably less than 0.5 mass %. In addition, the catalyst according to the first invention contains alumina preferably at 99.0 mass % or more, and more preferably at 99.25 mass % or more, and even more preferably at 99.5 mass % or more. Incidentally, the content of $SiO_2$ and alumina in the catalyst is a value measured by ICP emission spectroscopy (ICP-AES) using the Optima 8300 ICP-OES Spectrometer manufactured by PerkinElmer Co., Ltd.

EXAMPLES

Hereinafter, the invention will be specifically described with reference to Examples. However, the invention is not limited to these Examples.

Analysis of the raw material gas and the product was conducted by gas chromatography. The conversion ratio of isobutanol and the selectivity to isobutylene to be produced are respectively defined as follows.

Conversion ratio of isobutanol (%)=(β/α)×100

Selectivity to isobutylene (%)=(γ/δ)×100

α=number of moles of isobutanol supplied
β=number of moles of isobutanol reacted
γ=number of moles of isobutylene produced
δ=total number of moles of reaction product (isobutylene, isobutane, 1-butene, cis-2-butene, and trans-2-butene) detected by gas chromatography.

In addition, the weight hourly space velocity (WHSV) of isobutanol per unit time is defined as follows.

WHSV of isobutanol $(h^{-1})=e/f$ e=amount of isobutanol supplied per unit time (g/h)
f=amount of catalyst used (g).

Example 18

The reaction was conducted in the same manner as in Example 17 to be described later except that 16.0 g of a catalyst (mixed phase alumina of γ-alumina and θ-alumina, BET specific surface area: 105 $m^2/g$) molded in a cylindrical pellet shape (diameter: 1600 μm) was used as the catalyst and the flow rate of isobutanol and nitrogen gas was respectively changed to 40.1 mL/h and 40 mL (standard state)/min. Incidentally, 90 mass % or more of the catalyst had a particle size in a range of 700 μm or more and 10000 μm or less. At this time, the concentration of isobutanol supplied to the catalyst layer was 80.2 vol %, and the temperature in the catalyst layer during the reaction was 340° C. The WHSV under the present conditions was 2.01 $h^{-1}$, and the reaction pressure was 104 kPa as the absolute pressure.

Example 19

The reaction was conducted in the same manner as in Example 17 to be described later except that 16.0 g of a catalyst (mixed phase alumina of γ-alumina and θ-alumina, BET specific surface area: 105 $m^2/g$) molded in a cylindrical pellet shape (diameter: 3000 μm) was used as the catalyst and the flow rate of isobutanol and nitrogen gas was respectively changed to 40.1 mL/h and 40 mL (standard state)/min. Incidentally, 90 mass % or more of the catalyst had a particle size in a range of 700 μm or more and 10000 μm or less. At this time, the concentration of isobutanol supplied to the catalyst layer was 80.2 vol %, and the temperature in the catalyst layer during the reaction was 340° C. The WHSV under the present conditions was 2.01 $h^{-1}$, and the reaction pressure was 104 kPa as the absolute pressure.

Example 20

The reaction was conducted in the same manner as in Example 17 to be described later except that 16.0 g of a catalyst (mixed phase alumina of γ-alumina and θ-alumina, BET specific surface area: 105 m$^2$/g) molded in a cylindrical pellet shape (diameter: 4800 μm) was used as the catalyst and the flow rate of isobutanol and nitrogen gas was respectively changed to 40.1 mL/h and 40 mL (standard state)/min. Incidentally, 90 mass % or more of the catalyst had a particle size in a range of 700 μm or more and 10000 μm or less. At this time, the concentration of isobutanol supplied to the catalyst layer was 80.2 vol %, and the temperature in the catalyst layer during the reaction was 340° C. The WHSV under the present conditions was 2.01 h$^{-1}$, and the reaction pressure was 104 kPa as the absolute pressure.

The results for Examples 18 to 20 (reaction temperature: 340° C.) described above are presented in Table 7 and FIG. 7.

Example 21

The reaction was conducted in the same manner as in Example 18 except that 0.909 g of alumina (specific surface area: 105 m$^2$/g) which was crushed with an agate mortar, of which the particle size was then arranged to from 850 to 1190 μm, and which contained γ-alumina phase (γ-phase) and θ-alumina phase (0-phase) was used as the dehydration catalyst, the flow rate of isobutanol and nitrogen gas was respectively changed to 15.8 mL/h and 16 mL (standard state)/min, and the reaction pressure was adjusted before the recovery of reaction gas by attaching a back pressure valve. Incidentally, 90 mass % or more of the catalyst had a particle size in a range of 700 μM or more and 10000 μM or less. At this time, the concentration of isobutanol supplied to the catalyst layer was 79.9 vol %, and the temperature in the catalyst layer during the reaction was 340° C. The WHSV under the present conditions was 13.92 h$^{-1}$, and the reaction pressure was 105 kPa as the absolute pressure.

Example 22

The reaction was conducted in the same manner as in Example 21 except that the amount of the dehydration catalyst was changed to 0.912 g and the reaction pressure was adjusted to 140 kPa as the absolute pressure. At this time, the concentration of isobutanol supplied to the catalyst layer was 79.9 vol %, and the temperature in the catalyst layer during the reaction was 339° C. The WHSV under the present conditions was 13.88 h$^{-1}$.

Example 23

The reaction was conducted in the same manner as in Example 21 except that the reaction pressure was adjusted to 240 kPa as the absolute pressure. At this time, the concentration of isobutanol supplied to the catalyst layer was 79.9 vol %, and the temperature in the catalyst layer during the reaction was 339° C. The WHSV under the present conditions was 13.92 h$^{-1}$.

Example 24

The reaction was conducted in the same manner as in Example 21 except that the reaction pressure was adjusted to 289 kPa as the absolute pressure. At this time, the concentration of isobutanol supplied to the catalyst layer was 79.9 vol %, and the temperature in the catalyst layer during the reaction was 340° C. The WHSV under the present conditions was 13.92 h$^{-1}$.

Example 25

The reaction was conducted in the same manner as in Example 21 except that the amount of the dehydration catalyst was changed to 0.912 g and the reaction pressure was adjusted to 339 kPa as the absolute pressure. At this time, the concentration of isobutanol supplied to the catalyst layer was 79.9 vol %, and the temperature in the catalyst layer during the reaction was 339° C. The WHSV under the present conditions was 13.88 h$^{-1}$.

Example 26

The reaction was conducted in the same manner as in Example 21 except that the reaction pressure was adjusted to 392 kPa as the absolute pressure. At this time, the concentration of isobutanol supplied to the catalyst layer was 79.9 vol %, and the temperature in the catalyst layer during the reaction was 340° C. The WHSV under the present conditions was 13.92 h$^{-1}$.

Example 27

The reaction was conducted in the same manner as in Example 21 except that the reaction pressure was adjusted to 452 kPa as the absolute pressure. At this time, the concentration of isobutanol supplied to the catalyst layer was 79.9 vol %, and the temperature in the catalyst layer during the reaction was 339° C. The WHSV under the present conditions was 13.92 h$^{-1}$.

Example 28

The reaction was conducted in the same manner as in Example 21 except that the reaction pressure was adjusted to 550 kPa as the absolute pressure. At this time, the concentration of isobutanol supplied to the catalyst layer was 79.9 vol %, and the temperature in the catalyst layer during the reaction was 340° C. The WHSV under the present conditions was 14.04 h$^{-1}$.

Example 29

The reaction was conducted in the same manner as in Example 21 except that the reaction pressure was adjusted to 600 kPa as the absolute pressure. At this time, the concentration of isobutanol supplied to the catalyst layer was 79.9 vol %, and the temperature in the catalyst layer during the reaction was 340° C. The WHSV under the present conditions was 14.04 h$^{-1}$.

Example 30

The reaction was conducted in the same manner as in Example 21 except that the reaction pressure was adjusted to 692 kPa as the absolute pressure. At this time, the concentration of isobutanol supplied to the catalyst layer was 79.9 vol %, and the temperature in the catalyst layer during the reaction was 340° C. The WHSV under the present conditions was 13.89 h$^{-1}$.

The results for Examples 21 to 30 (reaction temperature: 339 to 340° C.) described above are presented in Table 8 and FIG. 8.

Examples of First Invention

Example 13

The catalyst was filled in a vertical tubular reaction tube having an inner diameter of 1.6 cm and a length of 50 cm.

As the catalyst, 2.29 g of crushed body of a catalyst (mixed phase alumina of θ-alumina and γ-alumina, particle size: 710 to 850 μm, BET specific surface area: 69 m$^2$/g, hereinafter, referred to as the catalyst A) molded in a cylindrical pellet shape (diameter: 3000 μm) was used. Incidentally, the proportion of the mixed phase alumina in the catalyst A was 99.5 mass % or more, and the content of SiO$_2$ therein was less than 0.5 mass %. In addition, 90 mass % or more of the catalyst A had a particle size in a range of 700 μm or more and 10000 μm or less. Isobutanol (manufactured by Nacalai Tesque, purity: 99.5 mass %) of the raw materials was supplied to the reactor equipped with the vertical tubular reaction tube filled with the catalyst via a vaporizer set to 200° C. The nitrogen gas as a diluent gas was supplied to the vaporizer and supplied to the reactor together with vaporized isobutanol. The WHSV (weight hourly space velocity per unit time) of isobutanol was 1.37 h$^{-1}$, and the temperature of the reactor was maintained at 344° C., and the pressure in the reactor was set to the atmospheric pressure. At this time, the concentration of isobutanol in the raw material gas supplied to the catalyst layer was 5.3 vol %, and the reaction temperature was 344° C. The reaction gas discharged through the reactor outlet was separated into a liquid phase portion and a gas phase portion. The gas phase portion was collected and subjected to the quantification of isobutylene, isobutane, 1-butene, cis-2-butene, and trans-2-butene. In addition, the liquid phase portion was collected and subjected to the quantification of isobutanol.

Example 14

The reaction was conducted in the same manner as in Example 13 except that 2.24 g of crushed body of a catalyst (mixed phase alumina of θ-alumina and γ-alumina, particle size: 710 to 850 μm, BET specific surface area: 105 m$^2$/g, hereinafter, referred to as the catalyst B) molded in a cylindrical pellet shape (diameter: 3000 μm) was used as the catalyst and the WHSV of isobutanol was changed to 1.40 h$^{-1}$. Incidentally, the proportion of the mixed phase alumina in the catalyst B was 99.5 mass % or more, and the content of SiO$_2$ therein was less than 0.5 mass %. In addition, 90 mass % or more of the catalyst B had a particle size in a range of 700 μm or more and 10000 μm or less.

Example 15

The reaction was conducted in the same manner as in Example 13 except that 1.00 g of crushed body of a catalyst (mixed phase alumina of δ-alumina and γ-alumina, particle size: 710 to 850 μm, BET specific surface area: 162 m$^2$/g, hereinafter, referred to as the catalyst C) molded in a cylindrical pellet shape (diameter: 1000 μm) was used as the catalyst and the WHSV of isobutanol was changed to 3.14 h$^{-1}$. Incidentally, the proportion of the mixed phase alumina in the catalyst C was 99.5 mass % or more, and the content of SiO$_2$ therein was less than 0.5 mass %. In addition, 90 mass % or more of the catalyst C had a particle size in a range of 700 μm or more and 10000 μm or less.

Comparative Example 9

The reaction was conducted in the same manner as in Example 13 except that 4.01 g of crushed body of a catalyst (mixed phase alumina of θ-alumina and γ-alumina, particle size: 710 to 850 μm, BET specific surface area: 44 m$^2$/g, hereinafter, referred to as the catalyst D) molded in a cylindrical pellet shape (diameter: 3000 μm) was used as the catalyst and the WHSV of isobutanol was changed to 0.78 h$^{-1}$. Incidentally, the proportion of the mixed phase alumina in the catalyst D was 99.5 mass % or more, and the content of SiO$_2$ therein was less than 0.5 mass %. In addition, 90 mass % or more of the catalyst D had a particle size in a range of 700 μm or more and 10000 μm or less.

Comparative Example 10

The reaction was conducted in the same manner as in Example 13 except that 1.00 g of crushed body of a catalyst (γ-alumina, particle size: 710 to 850 μm, BET specific surface area: 189 m$^2$/g, hereinafter, referred to as the catalyst E) molded in a cylindrical pellet shape (diameter: 1600 μm) was used as the catalyst and the WHSV of isobutanol was changed to 3.14 h$^{-1}$. Incidentally, the proportion of γ-alumina in the catalyst E was 99.5 mass % or more, and the content of SiO$_2$ therein was less than 0.5 mass %. In addition, 90 mass % or more of the catalyst E had a particle size in a range of 700 μm or more and 10000 μm or less.

The results for Examples 13 to 15 and Comparative Examples 9 and 10 (reaction temperature: 344° C.) described above are presented in Table 4 and FIG. 4.

Example 16

The reaction was conducted in the same manner as in Example 13 except that 20.0 g of a catalyst (mixed phase alumina of γ-alumina and θ-alumina, BET specific surface area: 105 m$^2$/g) molded in a cylindrical pellet shape (diameter: 1600 μm) was used as the catalyst and the flow rate of isobutanol and nitrogen gas was respectively changed to 23.4 mL/h and 40 mL (standard state)/min. Incidentally, 90 mass % or more of the catalyst had a particle size in a range of 700 μm or more and 10000 μm or less. At this time, the concentration of isobutanol supplied to the catalyst layer was 70.3 vol %, and the temperature in the catalyst layer during the reaction was 320° C. The WHSV under the present conditions was 0.94 h$^{-1}$, and the reaction pressure was 104 kPa as the absolute pressure.

Comparative Example 11

The reaction was conducted in the same manner as in Example 13 except that 12.7 g of a catalyst (mixed phase alumina of γ-alumina and θ-alumina, BET specific surface area: 189 m$^2$/g) molded in a cylindrical pellet shape (diameter: 1600 μm) was used as the catalyst and the flow rate of isobutanol and nitrogen gas was respectively changed to 40.9 mL/h and 70 mL (standard state)/min. Incidentally, 90 mass % or more of the catalyst had a particle size in a range of 700 μm or more and 10000 μm or less. At this time, the concentration of isobutanol supplied to the catalyst layer was 70.3 vol %, and the temperature in the catalyst layer during the reaction was 320° C. The WHSV under the present conditions was 2.59 h$^{-1}$, and the reaction pressure was 104 kPa as the absolute pressure.

Comparative Example 12

The reaction was conducted in the same manner as in Example 13 except that 15.0 g of a catalyst (alumina containing γ-alumina as the main component of the crystal layer, BET specific surface area: 200 m$^2$/g) molded in a cylindrical pellet shape (diameter: 1600 μm) was used as the catalyst and the flow rate of isobutanol and nitrogen gas was respectively changed to 58.4 mL/h and 101 mL (standard state)/min. Incidentally, 90 mass % or more of the catalyst had a particle size in a range of 700 μm or more and 10000 μm or less. At this time, the concentration of isobutanol supplied to the catalyst layer was 70.3 vol %, and the temperature in the catalyst layer during the reaction was 320° C. The WHSV under the present conditions was 3.13 h$^{-1}$, and the reaction pressure was 104 kPa as the absolute pressure.

The results for Example 16 and Comparative Examples 11 and 12 (reaction temperature: 320° C.) described above are presented in Table 5 and FIG. 5.

Example 17

The reaction was conducted in the same manner as in Example 13 except that 20.0 g of a catalyst (mixed phase alumina of γ-alumina and θ-alumina, BET specific surface area: 105 m$^2$/g) molded in a cylindrical pellet shape (diameter: 1600 μm) was used as the catalyst and the flow rate of isobutanol was changed to 23.9 mL/h. Incidentally, 90 mass % or more of the catalyst had a particle size in a range of 700 μm or more and 10000 μm or less. At this time, the concentration of isobutanol supplied to the catalyst layer was 100 vol %, and the temperature in the catalyst layer during the reaction was 320° C. The WHSV under the present conditions was 0.96 h$^{-1}$, and the reaction pressure was 104 kPa as the absolute pressure.

Comparative Example 13

The reaction was conducted in the same manner as in Example 17 except that 16.1 g of a catalyst (mixed phase alumina of γ-alumina and θ-alumina, BET specific surface area: 189 m$^2$/g) molded in a cylindrical pellet shape (diameter: 1600 μm) was used as the catalyst and the flow rate of isobutanol was changed to 32.1 mL/h. Incidentally, 90 mass % or more of the catalyst had a particle size in a range of 700 μm or more and 10000 μm or less. At this time, the concentration of isobutanol supplied to the catalyst layer was 100 vol %, and the temperature in the catalyst layer during the reaction was 320° C. The WHSV under the present conditions was 1.60 h$^{-1}$, and the reaction pressure was 104 kPa as the absolute pressure.

Comparative Example 14

The reaction was conducted in the same manner as in Example 17 except that 15.1 g of a catalyst (alumina containing γ-alumina as the main component of the crystal layer, BET specific surface area: 200 m$^2$/g) molded in a cylindrical pellet shape (diameter: 1600 μm) was used as the catalyst and the flow rate of isobutanol was changed to 58.4 mL/h. Incidentally, 90 mass % or more of the catalyst had a particle size in a range of 700 μm or more and 10000 μm or less. At this time, the concentration of isobutanol supplied to the catalyst layer was 100 vol %, and the temperature in the catalyst layer during the reaction was 320° C. The WHSV under the present conditions was 3.11 h$^{-1}$, and the reaction pressure was 103 kPa as the absolute pressure.

The results for Example 17 and Comparative Examples 13 and 14 (reaction temperature: 320° C.) described above are presented in Table 6 and FIG. 6.

Examples of Second Invention

Example 1

As the dehydration catalyst, 0.753 g of alumina (specific surface area: 209 m$^2$/g) which was crushed with an agate mortar, of which the particle size was then arranged to from 800 to 2000 pin, and which contained γ-alumina phase (γ-phase) as the main component of the crystal layer was used. Incidentally, 90 mass % or more of the catalyst had a particle size in a range of 700 pin or more and 10000 μm or less. With regard to the fixed bed reactor, the temperature in the catalyst layer was adjusted by using an electric furnace so that the temperature in the catalyst layer reached a predetermined temperature. Isobutanol (manufactured by Wako Pure Chemical Industries, Ltd., purity: 99.5 mass % or more, specific gravity: 0.803 g/mL) of the raw material was supplied to the evaporator set to 200° C. by using a microfeeder and adjusting the flow rate to 4.0 mL/h and evaporated therein. The nitrogen gas as a diluent gas was supplied to the evaporator at a flow rate of 37 mL (standard state)/min by using a mass flow meter and supplied to the reactor together with evaporated isobutanol. At this time, the concentration of isobutanol supplied to the catalyst layer was 30.3 vol %, and the temperature in the catalyst layer during the reaction (reaction temperature) was 300° C. The gas discharged through the reactor outlet side was collected and subjected to the quantification of isobutylene, isobutane, 1-butene, cis-2-butene, and trans-2-butene by gas chromatography. In addition, the reaction gas discharged through the reactor outlet side was trapped by using ice-cold acetonitrile and subjected to the quantification of isobutanol by gas chromatography. The reaction pressure gauge was installed in between the reactor inlet and the evaporator, and the pressure loss from the evaporator to the reactor inlet was so small as to be negligible in all the flow rate ranges under the conditions of Examples in this application. The WHSV under the present conditions was 4.27 h$^{-1}$ and the reaction pressure was 105 kPa as the absolute pressure.

Example 2

The reaction was conducted in the same manner as in Example 1 except that the amount of the dehydration catalyst was changed to 0.301 g and the flow rate of the nitrogen gas was changed to 16 mL (standard state)/min. At this time, the concentration of isobutanol supplied to the catalyst layer was 50.1 vol %, and the temperature in the catalyst layer during the reaction was 301° C. The WHSV under the present conditions was 10.67 h$^{-1}$, and the reaction pressure was 104 kPa as the absolute pressure.

Example 3

The reaction was conducted in the same manner as in Example 2 except that the flow rate of the nitrogen gas was changed to 7 mL (standard state)/min. At this time, the concentration of isobutanol supplied to the catalyst layer was 69.7 vol %, and the temperature in the catalyst layer during the reaction was 301° C. The WHSV under the present conditions was 10.67 h$^{-1}$, and the reaction pressure was 103 kPa as the absolute pressure.

Example 4

The reaction was conducted in the same manner as in Example 1 except that the amount of the dehydration catalyst was changed to 2.00 g and the flow rate of isobutanol and nitrogen gas was respectively changed to 8 mL/h and 6 mL (standard state)/min. At this time, the concentration of isobutanol supplied to the catalyst layer was 84.3 vol %, and the temperature in the catalyst layer during the reaction was 300° C. The WHSV under the present conditions was 3.21 h$^{-1}$, and the reaction pressure was 105 kPa as the absolute pressure.

Comparative Example 1

The reaction was conducted in the same manner as in Example 1 except that the amount of the dehydration catalyst was changed to 1.00 g and the flow rate of isobutanol and nitrogen gas was respectively changed to 3.7 mL/h and 280 mL (standard state)/min. At this time, the concentration of isobutanol supplied to the catalyst layer was 5.05 vol %, and the temperature in the catalyst layer during the reaction was 301° C. The WHSV under the present conditions was 2.97 h$^{-1}$, and the reaction pressure was 105 kPa as the absolute pressure.

Comparative Example 2

The reaction was conducted in the same manner as in Example 1 except that the amount of the dehydration catalyst was changed to 1.00 g and the flow rate of isobutanol and nitrogen gas was respectively changed to 2.2 mL/11 and 28 mL (standard state)/min. At this time, the concentration of isobutanol supplied to the catalyst layer was 24.0 vol %, and the temperature in the catalyst layer during the reaction was 300° C. The WHSV under the present conditions was 1.77 h$^{-1}$, and the reaction pressure was 104 kPa as the absolute pressure.

Comparative Example 3

The reaction was conducted in the same manner as in Example 1 except that the amount of the dehydration catalyst was changed to 1.00 g and the flow rate of isobutanol and nitrogen gas was respectively changed to 2.4 mL/h and 26 mL (standard state)/min. At this time, the concentration of isobutanol supplied to the catalyst layer was 27.1 vol %, and the temperature in the catalyst layer during the reaction was 300° C. The WHSV under the present conditions was 1.93 h$^{-1}$, and the reaction pressure was 103 kPa as the absolute pressure.

Comparative Example 4

The reaction was conducted in the same manner as in Example 1 except that the amount of the dehydration catalyst was changed to 1.00 g, the flow rate of isobutanol was changed to 3.5 mL/h, and the nitrogen gas was not supplied. At this time, the concentration of isobutanol supplied to the catalyst layer was 100 vol %, and the temperature in the catalyst layer during the reaction was 300° C. The WHSV under the present conditions was 2.81 h$^{-1}$, and the reaction pressure was 105 kPa as the absolute pressure.

The results for Examples 1 to 4 and Comparative Examples 1 to 4 (reaction temperature: 300 to 301° C.) described above are presented in Table 1 and FIG. 1.

Example 5

The reaction was conducted in the same manner as in Example 1 except that the amount of the dehydration catalyst was changed to 0.366 g and the flow rate of isobutanol and nitrogen gas was respectively changed to 5.0 mL/h and 16 mL (standard state)/min. At this time, the concentration of isobutanol supplied to the catalyst layer was 55.7 vol %, and the temperature in the catalyst layer during the reaction was 340° C. The WHSV under the present conditions was 10.97 h$^{-1}$, and the reaction pressure was 105 kPa as the absolute pressure.

Example 6

The reaction was conducted in the same manner as in Example 1 except that the amount of the dehydration catalyst was changed to 0.603 g, the flow rate of isobutanol and nitrogen gas was respectively changed to 8.0 mL/h and 11 mL (standard state)/min, and pure water was supplied to the evaporator set to 200° C. by using a micro-feeder and adjusting the flow rate to 0.7 mL/h. At this time, the concentration of isobutanol and water supplied to the catalyst layer was respectively 55.8 vol % and 25.2 vol %, and the temperature in the catalyst layer during the reaction was 340° C. The WHSV under the present conditions was 10.65 h$^{-1}$, and the reaction pressure was 104 kPa as the absolute pressure.

Example 7

The reaction was conducted in the same manner as in Example 1 except that the amount of the dehydration catalyst was changed to 0.345 g and the flow rate of isobutanol and nitrogen gas was respectively changed to 4.0 mL/h and 9 mL (standard state)/min. At this time, the concentration of isobutanol supplied to the catalyst layer was 64.1 vol %, and the temperature in the catalyst layer during the reaction was 340° C. The WHSV under the present conditions was 9.31 h$^{-1}$, and the reaction pressure was 105 kPa as the absolute pressure.

Example 8

The reaction was conducted in the same manner as in Example 1 except that the amount of the dehydration catalyst was changed to 0.608 g, the flow rate of isobutanol and nitrogen gas was respectively changed to 8.0 mL/h and 3 mL (standard state)/min, and pure water was supplied to the evaporator set to 200° C. by using a micro-feeder and adjusting the flow rate to 0.7 mL/h. At this time, the concentration of isobutanol and water supplied to the catalyst layer was respectively 64.8 vol % and 29.2 vol %, and the temperature in the catalyst layer during the reaction was 341° C. The WHSV under the present conditions was 10.57 h$^{-1}$, and the reaction pressure was 104 kPa as the absolute pressure.

Example 9

The reaction was conducted in the same manner as in Example 1 except that the amount of the dehydration catalyst was changed to 0.601 g and the flow rate of isobutanol and nitrogen gas was respectively changed to 8.0 mL/h and 11 mL (standard state)/min. At this time, the concentration of isobutanol supplied to the catalyst layer was 74.5 vol %, and the temperature in the catalyst layer during the reaction was 340° C. The WHSV under the present conditions was 10.69 h$^{-1}$, and the reaction pressure was 103 kPa as the absolute pressure.

Example 10

The reaction was conducted in the same manner as in Example 1 except that the amount of the dehydration catalyst was changed to 0.576 g and the flow rate of isobutanol and nitrogen gas was respectively changed to 8.0 mL/h and 6 mL (standard state)/min. At this time, the concentration of isobutanol supplied to the catalyst layer was 84.3 vol %, and the temperature in the catalyst layer during the reaction was 341° C. The WHSV under the present conditions was 11.15 h$^{-1}$, and the reaction pressure was 105 kPa as the absolute pressure.

Comparative Example 5

The reaction was conducted in the same manner as in Example 1 except that the amount of the dehydration catalyst was changed to 1.00 g, the flow rate of isobutanol was changed to 3.5 mL/h, and the nitrogen gas was not supplied. At this time, the concentration of isobutanol supplied to the catalyst layer was 21.3 vol %, and the temperature in the catalyst layer during the reaction was 340° C. The WHSV under the present conditions was 2.81 h$^{-1}$, and the reaction pressure was 105 kPa as the absolute pressure.

Comparative Example 6

The reaction was conducted in the same manner as in Example 1 except that the amount of the dehydration catalyst was changed to 0.543 g, the flow rate of isobutanol and nitrogen gas was respectively changed to 2.2 mL/h and 23 mL (standard state)/min, and pure water was supplied to the evaporator set to 200° C. by using a micro-feeder and adjusting the flow rate to 0.5 mL/h. At this time, the concentration of isobutanol and water supplied to the catalyst layer was respectively 21.0 vol % and 24.6 vol %, and the temperature in the catalyst layer during the reaction was 340° C. The WHSV under the present conditions was 3.25 h$^{-1}$, and the reaction pressure was 104 kPa as the absolute pressure.

Comparative Example 7

The reaction was conducted in the same manner as in Example 1 except that the amount of the dehydration catalyst was changed to 1.00 g, the flow rate of isobutanol was changed to 3.5 mL/h, and the nitrogen gas was not supplied. At this time, the concentration of isobutanol supplied to the catalyst layer was 100 vol %, and the temperature in the catalyst layer during the reaction was 340° C. The WHSV under the present conditions was 2.81 h$^{-1}$, and the reaction pressure was 105 kPa as the absolute pressure.

The results for Examples 5 to 10 and Comparative Examples 5 to 7 (reaction temperature: 340 to 341° C.) described above are presented in Table 2 and FIG. 2.

Example 11

The reaction was conducted in the same manner as in Example 1 except that the dehydration catalyst was changed to 4.00 g of alumina (BET specific surface area: 105 m$^2$/g) which was crushed with an agate mortar, of which the particle size was then arranged to from 850 to 2000 μm, and which contained γ-alumina phase (γ-phase) and θ-alumina phase (θ-phase) and the flow rate of isobutanol and nitrogen gas was respectively changed to 1.0 mL/h and 4 mL (standard state)/min. Incidentally, 90 mass % or more of the catalyst had a particle size in a range of 700 pin or more and 10000 μm or less. The concentration of isobutanol supplied to the catalyst layer was 50.0 vol %, and the temperature in the catalyst layer during the reaction was 340° C. The WHSV under the present conditions was 0.20 h$^{-1}$, and the reaction pressure was 104 kPa as the absolute pressure.

Example 12

The reaction was conducted in the same manner as in Example 11 except that the amount of the dehydration catalyst was changed to 4.50 g. At this time, the concentration of isobutanol supplied to the catalyst layer was 50.0 vol %, and the temperature in the catalyst layer during the reaction was 340° C. The WHSV under the present conditions was 0.18 h$^{-1}$, and the reaction pressure was 105 kPa as the absolute pressure.

Comparative Example 8

The reaction was conducted in the same manner as in Example 11 except that the amount of the dehydration catalyst was changed to 5.00 g. At this time, the concentration of isobutanol supplied to the catalyst layer was 50.0 vol %, and the temperature in the catalyst layer during the reaction was 340° C. The WHSV under the present conditions was 0.16 h$^{-1}$, and the reaction pressure was 104 kPa as the absolute pressure.

The results for Examples 11 and 12 and Comparative Example 8 (reaction temperature: 340° C.) described above are presented in Table 3 and FIG. 3.

TABLE 1

| | | Reaction temperature ° C. | Reaction pressure kPa | Particle size of catalyst μm | Concentration of IBA vol % | WHSV h$^{-1}$ | Conversion ratio of isobutanol % | Selectivity Isobutane % | 1-butene % | Isobutylene % | Cis-2-butene % | Trans-2-butene % |
|---|---|---|---|---|---|---|---|---|---|---|---|---|
| Example | 1 | 300 | 105 | 800-2000 | 30.3 | 4.27 | 98.97 | 0.03 | 1.10 | 97.19 | 1.17 | 0.52 |
| | 2 | 301 | 104 | 800-2000 | 50.1 | 10.67 | 95.11 | 0.06 | 1.03 | 97.77 | 0.60 | 0.55 |
| | 3 | 301 | 103 | 800-2000 | 69.7 | 10.67 | 98.40 | 0.06 | 1.02 | 98.25 | 0.40 | 0.28 |
| | 4 | 300 | 105 | 800-2000 | 84.3 | 3.21 | 98.82 | 0.04 | 0.91 | 97.94 | 0.74 | 0.37 |
| Comparative Example | 1 | 301 | 105 | 800-2000 | 5.05 | 2.97 | 98.14 | 0.01 | 1.55 | 95.10 | 2.24 | 1.09 |
| | 2 | 300 | 104 | 800-2000 | 24.0 | 1.77 | 97.89 | 0.04 | 1.42 | 95.04 | 2.35 | 1.15 |
| | 3 | 300 | 103 | 800-2000 | 27.1 | 1.93 | 98.20 | 0.03 | 1.33 | 95.56 | 2.10 | 0.98 |
| | 4 | 300 | 105 | 800-2000 | 100 | 2.81 | 96.00 | 0.06 | 1.05 | 96.66 | 1.22 | 1.01 |

TABLE 2

|  |  | Reaction temperature ° C. | Reaction pressure kPa | Particle size of catalyst μm | Concentration of IBA vol % | Concentration of water supplied vol % | WHSV h⁻¹ | Conversion ratio of isobutanol % | Selectivity | | | | |
|---|---|---|---|---|---|---|---|---|---|---|---|---|---|
|  |  |  |  |  |  |  |  |  | Isobutane % | 1-butene % | Isobutylene % | Cis-2-butene % | Trans-2-butene % |
| Example | 5 | 340 | 105 | 800-2000 | 55.7 | — | 10.97 | 98.17 | 0.02 | 1.35 | 96.16 | 1.78 | 0.68 |
|  | 6 | 340 | 104 | 800-2000 | 55.8 | 25.20 | 10.65 | 95.23 | 0.03 | 1.22 | 96.98 | 1.18 | 0.59 |
|  | 7 | 340 | 105 | 800-2000 | 64.1 | — | 9.31 | 97.57 | 0.02 | 1.31 | 96.66 | 1.38 | 0.62 |
|  | 8 | 341 | 104 | 800-2000 | 64.8 | 29.20 | 10.57 | 96.56 | 0.03 | 1.17 | 97.23 | 1.03 | 0.54 |
|  | 9 | 340 | 103 | 800-2000 | 74.5 | — | 10.69 | 95.44 | 0.03 | 1.29 | 96.77 | 1.27 | 0.65 |
|  | 10 | 341 | 105 | 800-2000 | 84.3 | — | 11.15 | 99.47 | 0.07 | 1.30 | 96.52 | 1.46 | 0.65 |
| Comparative Example | 5 | 340 | 105 | 800-2000 | 21.3 | — | 2.81 | 99.80 | 0.03 | 2.15 | 94.09 | 2.57 | 1.14 |
|  | 6 | 340 | 104 | 800-2000 | 21.0 | 24.60 | 3.25 | 95.56 | 0.02 | 1.72 | 94.53 | 2.30 | 1.44 |
|  | 7 | 340 | 105 | 800-2000 | 100 | — | 2.81 | 100 | 0.03 | 1.08 | 94.48 | 1.94 | 2.47 |

TABLE 3

|  |  | Reaction temperature ° C. | Reaction pressure kPa | Particle size of catalyst μm | Concentration of IBA vol % | WHSV h⁻¹ | Conversion ratio of isobutanol % | Selectivity | | | | |
|---|---|---|---|---|---|---|---|---|---|---|---|---|
|  |  |  |  |  |  |  |  | Isobutane % | 1-butene % | Isobutylene % | Cis-2-butene % | Trans-2-butene % |
| Example | 11 | 340 | 104 | 850-2000 | 50.0 | 0.20 | 99.99 | 0.04 | 1.96 | 95.31 | 2.08 | 0.62 |
|  | 12 | 340 | 105 | 850-2000 | 50.0 | 0.18 | 99.90 | 0.05 | 1.98 | 95.14 | 2.13 | 0.71 |
| Comparative Example | 8 | 340 | 104 | 850-2000 | 50.0 | 0.16 | 100 | 0.07 | 2.33 | 94.24 | 2.58 | 0.78 |

TABLE 4

|  |  | Specific surface area m²/g | Reaction temperature ° C. | Reaction pressure kPa | Particle size of catalyst μm | Concentration of IBA vol % | WHSV h⁻¹ | Conversion ratio of isobutanol % | Selectivity | | | | |
|---|---|---|---|---|---|---|---|---|---|---|---|---|---|
|  |  |  |  |  |  |  |  |  | Isobutane % | 1-butene % | Isobutylene % | Cis-2-butene % | Trans-2-butene % |
| Example | 13 | 69 | 344 | 104 | 710-850 | 5.3 | 1.37 | 100 | 0.25 | 4.13 | 87.10 | 4.53 | 3.96 |
|  | 14 | 105 | 344 | 104 | 710-850 | 5.3 | 1.40 | 100 | 0.26 | 4.06 | 87.60 | 4.58 | 3.51 |
|  | 15 | 162 | 344 | 103 | 710-850 | 5.3 | 3.14 | 100 | 0.36 | 4.05 | 87.00 | 4.70 | 3.92 |
| Comparative Example | 9 | 44 | 344 | 103 | 710-850 | 5.3 | 0.78 | 100 | 0.37 | 4.57 | 84.00 | 5.35 | 5.67 |
|  | 10 | 189 | 344 | 104 | 710-850 | 5.3 | 3.14 | 100 | 0.34 | 4.57 | 83.00 | 5.98 | 6.09 |

TABLE 5

|  |  | Specific surface area m²/g | Reaction temperature ° C. | Reaction pressure kPa | Particle size of catalyst μm | Concentration of IBA vol % | WHSV h⁻¹ | Conversion ratio of isobutanol % | Selectivity | | | | |
|---|---|---|---|---|---|---|---|---|---|---|---|---|---|
|  |  |  |  |  |  |  |  |  | Isobutane % | 1-butene % | Isobutylene % | Cis-2-butene % | Trans-2-butene % |
| Example | 16 | 105 | 320 | 104 | 1600 | 70.3 | 0.94 | 99.30 | 0.10 | 2.09 | 94.89 | 2.06 | 0.86 |
| Comparative Example | 11 | 189 | 320 | 104 | 1600 | 70.3 | 2.59 | 100 | 0.11 | 2.20 | 94.13 | 2.51 | 1.05 |
|  | 12 | 200 | 320 | 104 | 1600 | 70.3 | 3.13 | 97.45 | 0.14 | 2.14 | 94.27 | 2.5 | 0.96 |

TABLE 6

| | | Specific surface area m²/g | Reaction temperature °C | Reaction pressure kPa | Particle size of catalyst μm | Concentration of IBA vol % | WHSV h⁻¹ | Conversion ratio of isobutanol % | Selectivity | | | | |
|---|---|---|---|---|---|---|---|---|---|---|---|---|---|
| | | | | | | | | | Isobutane % | 1-butene % | Isobutylene % | Cis-2-butene % | Trans-2-butene % |
| Example | 17 | 105 | 320 | 104 | 1600 | 100 | 0.96 | 98.12 | 0.10 | 1.73 | 95.60 | 1.98 | 0.59 |
| Comparative Example | 13 | 189 | 320 | 104 | 1600 | 100 | 1.60 | 97.66 | 0.13 | 2.01 | 93.40 | 2.96 | 1.50 |
| | 14 | 200 | 320 | 103 | 1600 | 100 | 3.11 | 97.43 | 0.13 | 2.01 | 93.60 | 2.88 | 1.34 |

TABLE 7

| | | Specific surface area m²/g | Reaction temperature °C | Reaction pressure kPa | Particle size of catalyst μm | Concentration of IBA vol % | WHSV h⁻¹ | Conversion ratio of isobutanol % | Selectivity | | | | | Yield of isobutylene % |
|---|---|---|---|---|---|---|---|---|---|---|---|---|---|---|
| | | | | | | | | | Isobutane % | 1-butene % | Isobutylene % | Cis-2-butene % | Trans-2-butene % | |
| Example | 18 | 105 | 340 | 104 | 1600 | 80.2 | 2.01 | 99.70 | 0.11 | 2.23 | 94.64 | 2.23 | 0.80 | 94.35 |
| Example | 19 | 105 | 340 | 104 | 3000 | 80.2 | 2.01 | 96.88 | 0.12 | 4.11 | 90.14 | 4.11 | 1.51 | 87.33 |
| Example | 20 | 105 | 340 | 104 | 4800 | 80.2 | 2.01 | 87.97 | 0.11 | 2.36 | 94.22 | 2.36 | 0.95 | 82.89 |

TABLE 8

| | | | Specific surface area m²/g | Reaction temperature °C | Reaction pressure kPa | Particle size of catalyst μm | Concentration of IBA vol % | WHSV h⁻¹ | Conversion ratio of isobutanol % |
|---|---|---|---|---|---|---|---|---|---|
| Example | 21 | SA-3177 | 105 | 340 | 105 | 850-1190 | 79.9 | 13.92 | 82.42 |
| | 22 | SA-3177 | 105 | 339 | 140 | 850-1190 | 79.9 | 13.88 | 78.87 |
| | 23 | SA-3177 | 105 | 339 | 240 | 850-1190 | 79.9 | 13.92 | 74.41 |
| | 24 | SA-3177 | 105 | 340 | 289 | 850-1190 | 79.9 | 13.92 | 74.58 |
| | 25 | SA-3177 | 105 | 339 | 339 | 850-1190 | 79.9 | 13.88 | 66.92 |
| | 26 | SA-3177 | 105 | 340 | 392 | 850-1190 | 79.9 | 13.92 | 69.57 |
| | 27 | SA-3177 | 105 | 339 | 452 | 850-1190 | 79.9 | 13.92 | 65.91 |
| | 28 | SA-3177 | 105 | 340 | 550 | 850-1190 | 79.9 | 14.04 | 59.90 |
| | 29 | SA-3177 | 105 | 340 | 600 | 850-1190 | 79.9 | 14.04 | 60.87 |
| | 30 | SA-3177 | 105 | 340 | 692 | 850-1190 | 79.9 | 13.89 | 58.72 |

| | | | Selectivity | | | | | Yield of isobutylene % |
|---|---|---|---|---|---|---|---|---|
| | | | Isobutane % | 1-butene % | Isobutylene % | Cis-2-butene % | Trans-2-butene % | |
| Example | 21 | SA-3177 | 0.04 | 2.10 | 94.96 | 2.23 | 0.67 | 78.27 |
| | 22 | SA-3177 | 0.04 | 1.99 | 95.36 | 1.99 | 0.62 | 75.21 |
| | 23 | SA-3177 | 0.05 | 1.90 | 95.59 | 1.90 | 0.55 | 71.13 |
| | 24 | SA-3177 | 0.05 | 1.87 | 95.64 | 1.90 | 0.54 | 71.33 |
| | 25 | SA-3177 | 0.06 | 1.84 | 95.73 | 1.84 | 0.53 | 64.07 |
| | 26 | SA-3177 | 0.06 | 1.84 | 95.73 | 1.85 | 0.52 | 66.60 |
| | 27 | SA-3177 | 0.06 | 1.82 | 95.79 | 1.82 | 0.52 | 63.14 |
| | 28 | SA-3177 | 0.06 | 1.75 | 96.02 | 1.71 | 0.53 | 57.52 |
| | 29 | SA-3177 | 0.06 | 1.72 | 96.04 | 1.70 | 0.53 | 58.46 |
| | 30 | SA-3177 | 0.07 | 1.91 | 95.55 | 1.90 | 0.65 | 56.11 |

As presented in Tables 1 to 6, it was possible to produce isobutylene from isobutanol at a high selectivity in Examples 1 to 17. On the other hand, the selectivity to isobutylene in Comparative Examples 1 to 14 was inferior to Examples 1 to 17. In addition, as presented in Tables 7 and 8, it was possible to produce isobutylene from isobutanol in a high yield in Examples 18 to 30.

This application is based upon and claims the benefit of priority of the prior Japanese Patent Application No. 2014-095675 filed on May 7, 2014 and the prior Japanese Patent Application No. 2014-167032 filed on Aug. 20, 2014, the entire contents of which are incorporated herein by reference.

The invention of this application has been described with reference to embodiments and examples, but the invention of this application is not limited to the embodiments and examples described above. The configuration or details of the invention of this application can be changed in various ways to be understood by those skilled in the art within the scope of the invention of this application.

INDUSTRIAL APPLICABILITY

Isobutylene obtained by the invention is one of the important chemical raw materials that are converted into, for example, ethyl tert-butyl ether (ETBE), paraxylene, and a methyl methacrylate (MMA) monomer. Among these, for example, the MMA monomer is a substance with significantly high utility value as a raw material for poly(methyl methacrylate) that is useful as a transparent resin.

The invention claimed is:

1. A method for producing isobutylene comprising:
   introducing a reaction gas containing isobutanol into a reactor, wherein the reaction gas further contains water in a content of 0.1 to 70 vol %; and
   dehydrating the isobutanol,
   at a reaction pressure of 50 kPa or more and 750 kPa or less as an absolute pressure,
   by using an alumina catalyst having a BET specific surface area in a range of 60 $m^2/g$ or more and 175 $m^2/g$ or less and having a content of $SiO_2$ of less than 1.0 mass %.

2. The method for producing isobutylene according to claim 1, wherein 90 mass % or more of the alumina catalyst has a particle size in a range of 700 μm or more and 10000 μm or less and
   a weight hourly space velocity (WHSV) of isobutanol entering a reaction zone to be supplied is 0.175 $h^{-1}$ or more and 20 $h^{-1}$ or less.

3. The method for producing isobutylene according to claim 1, wherein the BET specific surface area of the alumina catalyst is in a range of 65 $m^2/g$ or more and 170 $m^2/g$ or less.

4. The method for producing isobutylene according to claim 1, wherein the BET specific surface area of the alumina catalyst is in a range of 69 $m^2/g$ or more and 162 $m^2/g$ or less.

5. The method for producing isobutylene according to claim 1, wherein the reaction pressure is 75 kPa or more and 700 kPa or less as an absolute pressure.

6. The method for producing isobutylene according to claim 1, wherein the reaction pressure is 100 kPa or more and 650 kPa or less as an absolute pressure.

7. The method for producing isobutylene according to claim 1, wherein a temperature of the dehydration is in a range of from 108 to 500° C.

8. The method for producing isobutylene according to claim 1, wherein a temperature of the dehydration is in a range of from 150 to 400° C.

9. The method for producing isobutylene according to claim 1, wherein the content of $SiO_2$ in the alumina catalyst is less than 0.5 mass %.

10. A method for producing isobutylene comprising:
    introducing a reaction gas containing isobutanol into a reactor, wherein the reaction gas further contains water in a content of 0.1 to 70 vol %; and
    dehydrating the isobutanol,
    at a concentration of isobutanol relative to all gaseous components entering a reaction zone to be supplied of 30 vol % or more and 85 vol % or less,
    a weight hourly space velocity (WHSV) of isobutanol of 0.175 $h^{-1}$ or more and 20 $h^{-1}$ or less, and
    a reaction pressure of 50 kPa or more and 750 kPa or less as an absolute pressure,
    by using an alumina catalyst of which 90 mass % or more has a particle size in a range of 700 μm or more and 10000 μm or less.

11. The method for producing isobutylene according to claim 10, wherein the concentration of isobutanol is 55 vol % or more and 80 vol % or less.

12. The method for producing isobutylene according to claim 10, wherein the weight hourly space velocity (WHSV) of isobutanol is 0.2 $h^{-1}$ or more and 18 $h^{-1}$ or less.

13. The method for producing isobutylene according to claim 10, wherein the weight hourly space velocity (WHSV) of isobutanol is 0.25 $h^{-1}$ or more and 16 $h^{-1}$ or less.

14. The method for producing isobutylene according to claim 10, wherein a temperature of the dehydration is in a range of from 108 to 500° C.

15. The method for producing isobutylene according to claim 10, wherein a temperature of the dehydration is in a range of from 150 to 400° C.

* * * * *